United States Patent
Boswell et al.

(10) Patent No.: US 6,680,398 B1
(45) Date of Patent: Jan. 20, 2004

(54) METHOD OF MAKING MERCAPTOALKYLALKOXYSILANES

(75) Inventors: Lisa Marie Boswell, Auburn, MI (US); William Charles Maki, Midland, MI (US); Anil Kumar Tomar, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/219,080

(22) Filed: Aug. 16, 2002

(51) Int. Cl.$^7$ .................................................. C07F 7/08
(52) U.S. Cl. ........................................ 556/429; 556/427
(58) Field of Search ................................. 556/427, 429

(56) References Cited

U.S. PATENT DOCUMENTS

| | | | |
|---|---|---|---|
| 3,590,065 A | 6/1971 | Rakus et al. | 260/448.8 |
| 3,849,471 A | 11/1974 | Omietanski et al. | 260/448.2 |
| 3,890,213 A | 6/1975 | Louthan | 204/158 |
| 5,405,985 A | 4/1995 | Parker et al. | 556/427 |
| 5,583,245 A | 12/1996 | Parker et al. | 556/427 |
| 5,840,952 A | 11/1998 | Kudo et al. | 556/429 |
| 6,384,256 B1 | 5/2002 | Backer et al. | 556/427 |

FOREIGN PATENT DOCUMENTS

| | | | |
|---|---|---|---|
| WO | 1102251 | 2/1965 | B44D/1/34 |

*Primary Examiner*—Samuel Barts
(74) *Attorney, Agent, or Firm*—Jim L. DeCesare

(57) ABSTRACT

In a first embodiment of a process for making mercaptoalkylalkoxysilanes, a pH adjusting agent and a sulfide containing compound are mixed in an aqueous phase to provide a pH of 4–9, a phase transfer catalyst is added to the aqueous phase, a haloalkylalkoxysilane is then added to the aqueous phase to form a reaction mixture containing mercaptoalkylalkoxysilanes and water soluble byproducts, and the desired mercaptoalklyalkoxysilanes are separated from the water soluble byproducts. In an alternate embodiment, the haloalkylalkoxysilane, the phase transfer catalyst, and an anhydrous pH adjusting agent such as sulfur dioxide, carbon dioxide, hydrogen sulfide, phosphoric acid, boric acid, and hydrochloric acid, are mixed, then an aqueous solution of a sulfide containing compound is added to form a reaction mixture containing mercaptoalkylalkoxysilanes and water soluble byproducts, and desired mercaptoalklyalkoxysilanes are separated from water soluble byproducts.

42 Claims, No Drawings

METHOD OF MAKING MERCAPTOALKYLALKOXYSILANES

FIELD OF THE INVENTION

This invention relates to the synthesis of mercapto-functional organosilicon compounds $\equiv$Si—(CH$_2$)$_n$SH, more particularly mercaptoalkylalkoxysilanes such as mercaptopropyltrialkoxy silane (MPTAS), using phase transfer catalysts. The process is capable of producing high purity mercaptopropyltriethoxysilane (MPTES), for example. Mercaptoalkylalkoxysilanes made by the process generally have a formula corresponding to Z—Alk—SH in which Z is one of a group consisting of —SiR$^1{}_2$R$^2$, —SiR$^1$R$^2{}_2$, and —SiR$^2{}_3$; in which R$^1$ is an alkyl group with 1–12 carbon atoms, a cyclohexyl group, or a phenyl group; R$^2$ is an alkoxy group containing 1–12 carbon atoms; and Alk represents a divalent hydrocarbon radical having 1–18 carbon atoms and containing no unsaturation.

BACKGROUND OF THE INVENTION

Sulfur containing organosilicon compounds are known to be useful as reactive coupling agents between rubber and silica fillers, for improving the properties of cured rubber. They are also known to be useful as adhesion promoters, for adhering rubber compositions to substrates such as glass and metal. However, many sulfur containing organosilicon compounds are difficult to make in good yield, because undesirable byproducts are produced from various side reactions occurring when traditional methods are employed.

For example, U.S. Pat. No. 3,590,065 (Jun. 29, 1971) relates to a reaction between a haloalkylalkoxysilane and a thio-urea in the presence of ammonia. However, the necessity of handling bulky by-products such as guanidine hydrochloride is the major disadvantage associated with this particular method.

U.S. Pat. No. 3,849,471 (Nov. 19, 1974) is directed to another method involving reactions between haloalkylalkoxysilanes and hydrogen sulfide gas in the presence of amines. However, this reaction is carried out under a high pressure, and also has the disadvantage of producing a fluffy by-product salt which is difficult to filter from the end product.

U.S. Pat. No. 3,890,213 (Jun. 17, 1975) relates to yet another method involving reactions between hydrogen sulfide and alkenylalkoxysilanes. However, the major disadvantage associated with this method is that the mercaptosilane product itself can become associated with the alkenylalkoxysilane to form copious amounts of sulfide side products.

In British Patent 1,102,251 (Feb. 7, 1968), a method is described involving the reaction of sodium methoxide and hydrogen sulfide to produce sodium hydrosulfide, which is then further reacted with an haloalkylalkoxysilane. The disadvantage associated with this particular method however, is that the reaction of sodium methoxide with H$_2$S produces sodium sulfide as a by-product, which in turn leads to large amounts of polysulfide silanes in the end product.

U.S. Pat. No. 5,583,245 ((Dec. 10, 1996) describes a process for making compounds generally corresponding to the formula Z—Alk—S$_n$—Alk—Z, in which Z and Alk are the same as defined above, and in which n is 2–8. According to the process in the '245 patent, a compound of the formula Z—Alk—X where X is chlorine or bromine, is reacted with an ammonium hydrosulfide or an alkali metal hydrosulfide, and sulfur, using a phase transfer catalyst, in an aqueous phase.

The '245 patent teaches that an additional reactant corresponding to Alk—X may be present, where an unsymmetrical compound corresponding to Alk—S—$_{Alk—Z}$ is desired, in addition to bis type end products. While the '245 patent does describe a method for preparing MPTES in a 64.9% yield by reacting (i) sodium hydrosulfide flakes and (ii) chloropropyltriethoxysilane (CPTES), in a saturated sodium chloride solution and toluene solvent, in the presence of a phase transfer catalyst, the yield of MPTES was not optimal.

While U.S. Pat. No. 5,840,952 ((Nov. 24, 1998) describes a method of making mercaptopropylalkoxysilanes in good yield, by purging hydrogen sulfide gas in a sodium sulfide solution in methanol, and then reacting it with chloropropyltrimethoxysilane (CPTMS) in an anhydrous system, the disadvantage associated with this process is that sodium sulfide used must first be dehydrated. Another disadvantage of the '952 patent is that it requires the use of high pressure, i.e., 600 psi/4,140 kilopascal (kPa) hydrogen sulfide gas, to reduce sodium sulfide to sodium hydrosulfide.

In a prior copending application assigned to the same assignee as the present invention, i.e., U.S. patent application Ser. No. 09/895,719, filed Jun. 29, 2001, and entitled "Preparation of Sulfur Containing Organosilicon Compounds Using a Buffered Phase Transfer Catalysis Process", there is described a process based on phase transfer catalysis. However, this process is directed to the production of bis-type sulfido silanes $\equiv$Si—S—Si$\equiv$, which generally correspond to the formula (RO)$_{3-m}$R$_m$Si—Alk—S$_n$—Alk—SiR$_m$(OR)$_{3-m}$, wherein R is a monovalent hydrocarbon group with 1–12 carbon atoms; Alk represents a divalent hydrocarbon group with 1–18 carbon atoms; m is 0–2; and n is 1–8. According to the process described in the copending application, (A) a sulfide compound M$_2$S$_n$ or MHS wherein H is hydrogen, M is ammonium or an alkali metal, and n is as defined above, is reacted with (B) a silane compound corresponding to (RO)$_{3-m}$R$_m$Si—Alk—X, wherein X is Cl, Br or I, m is the same as defined above, and (C) sulfur, in the presence of a phase transfer catalyst, in an aqueous phase containing a buffering agent. However, no method is described in the copending application for making mercapto-functional organosilicon compounds, i.e., compounds containing the group $\equiv$Si—(CH$_2$)$_n$SH.

The copending application, however, results in sulfidosilanes instead of mercaptosilanes. This is because of the presence of elemental sulfur in the copending application, and the use of different buffering agents in the copending application than the buffering agents (i.e., pH adjusting agents) used in the present application. In addition, pH is a controlling factor in these applications as to what is being prepared. The difference is based on (i) establishment of the equilibrium

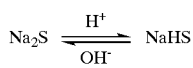

or (ii) the equilibrium

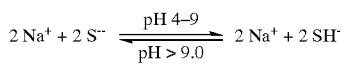

and (iii) the fact that the disulfide anion is undetectable at a pH of about 9 or less.

Another way to view the difference is that when it is desired to make mercaptosilanes, rather than sulfidosilanes, the alkalinity of the reaction mixture must remain at a pH in the range of 4 to 9. Higher concentrations of alkalinity lead to disulfide anion formation from the mercaptide anion already present, without adding elemental sulfur. When it is desired to make the disulfide, it is necessary for the system to remain high in alkalinity, to inhibit any equilibrium leading to NaHS formation. As these reactants naturally react and form a neutral NaCl, the alkalinity of the brine will lessen over time, and can become low enough so that SH will form.

So the present application differs from the copending application in that (i) different pH adjusting agents are employed, (ii) the pH is different, i.e., a pH of 4 to 9, preferably a pH of 5–8, and more preferably a pH of 5 to less than 7, instead of a pH of 7–14, and (iii) the order of addition of the reactants is not the same. The result is that at the lower pH of 4 to less than 7, any sulfide present is converted to mercaptan in the aqueous phase.

The process of the present invention further differs from processes described above, in that it is capable of providing high yields of mercaptosilanes under mild conditions, without the use of solvents, toxic gas, and strictly anhydrous conditions. In addition, it is more economical, environment friendly, and capable of utilizing relatively inexpensive starting materials. When there is any byproduct present, it is simply an alkali metal salt, which can be easily removed by dissolution during the water and phase separation sequence of the process.

Other advantages provided by the present invention over the prior art include the benefit that the mercaptoalkylalkoxy silane yield is significantly increased when chloroalkylalkoxysilanes are reacted with an aqueous solution of sodium hydrosulfide in the presence of (i) a phase transfer catalyst and (ii) gases which form an acidic solution in water to control the pH of the aqueous phase, at a pressure of 10–200 psi/69–1,380 kPa, preferably 25–100 psi/173–690 kPa. Some particularly suitable gases are hydrogen sulfide, carbon dioxide, and sulfur dioxide. The reaction can be carried out without requiring use of a solvent, and no extra salt is needed to saturate the aqueous phase to prevent hydrolysis of any alkoxy groups present on silicon atoms in the molecule.

Most significantly, however, the order of addition of the reactants plays an important role in the product yield and quality. Thus, it was surprising to discover that the mercaptoalkylalkoxysilane yield can be increased when the NaHS solution is added to a mixture of the haloalkylalkoxysilane and the anhydrous phase transfer catalyst at the reaction temperature. In this regard, anhydrous pH adjusting salts may be required to be added to the organic reaction mixture before the NaHS addition, to control any potential side reactions. In those instances where it is desired to carry out the reaction under pressure conditions, the reactor is pressurized with $H_2S$, $CO_2$, and/or $SO_2$, before addition of the NaHS to the haloalkylalkoxysilane/catalyst mixture. The anhydrous salt of a mineral acid and the phase transfer catalyst can then be mixed with the haloalkylalkoxysilane, before adding the sodium hydrosulfide. This feature will tend to minimize any hydrolysis of alkoxy groups on silicon.

Lastly, the presence of side products of species such as 3,3'bis(triethoxysilylpropyl)monosulfide (TESPM) and 3,3'bis(triethoxysilylpropyl)disulfide (TESPD), are significantly reduced when mineral acids and their salts are used in the process. Thus, the acids and the pH adjusting agents having pH values of less than seven, react with disodium sulfide impurities in the aqueous solution of sodium hydrosulfide, and produce sodium hydrosulfide and hydrogen sulfide gas. The maintenance of a positive pressure of $H_2S$ in the existing headspace will prevent the formation of the sulfide species, by shifting the equilibrium between NaHS and sodium sulfide ($Na_2S$), toward NaHS in the aqueous phase.

SUMMARY OF THE INVENTION

This invention is directed to a process for making high purity mercaptoalkylalkoxysilanes using a phase transfer catalyst, by forming a mixture of (i) an haloalkylalkoxysilane and (ii) a phase transfer catalyst, prior to the addition of (iii) a sulfide compound such as sodium hydrosulfide. The reaction will occur without requiring that there be present in the haloalkylalkoxysilane phase, a concentrated sodium chloride salt solution with the sodium hydrosulfide, or an organic solvent. The formation of byproducts can also be reduced by the addition of certain pH adjusting agents having a pH of less than seven to the mixture containing the haloalkylalkoxysilane and the phase transfer catalyst. In particular, the process is directed to the reaction of an aqueous solution of sodium hydrosulfide with CPTES in the presence of a phase transfer catalyst, and a pH adjusting agent of a pH of 4 to 9, preferably a pH of 5–8, and more preferably a pH of 5 to less than 7. Thus, it was surprisingly discovered that both the order of addition of the reactants, and the addition of certain pH adjusting agents in the reaction mixture, significantly increased the yield of MPTES by minimizing formation of undesirable end products such as TESPM and TESPD.

As an additional feature, the invention is directed to the use of certain pH adjusting agents which are acidic in their nature in an aqueous solution, such as $SO_2$ (sulfur dioxide), $CO_2$ (carbon dioxide), $H_2S$ (hydrogen sulfide), $H_3PO_4$ (phosphoric acid), $H_3BO_3$ (boric acid), and HCl (hydrochloric acid). These materials improve the yield by minimizing the production of any undesirable byproduct such as TESPM and TESPD.

In a first embodiment of the process for making the mercaptoalkylalkoxysilanes, a pH adjusting agent and a sulfide containing compound are mixed in an aqueous phase to provide a pH of 4–9, a phase transfer catalyst is added to the aqueous phase, a haloalkylalkoxysilane is then added to the aqueous phase to form a reaction mixture containing mercaptoalkylalkoxysilanes and water soluble byproducts, and the desired mercaptoalklyalkoxysilanes are separated from the water soluble byproducts.

In an alternate embodiment, the haloalkylalkoxysilane, the phase transfer catalyst, and an anhydrous pH adjusting agent such as sulfur dioxide, carbon dioxide, hydrogen sulfide, phosphoric acid, boric acid, and hydrochloric acid, and anhydrous salts thereof, are mixed, then an aqueous solution of a sulfide containing compound is added to form a reaction mixture containing mercaptoalkylalkoxysilanes and water soluble byproducts, and desired mercaptoalklyalkoxysilanes are separated from water soluble byproducts.

Following is a list of acronyms used in this application:
CPTES—Chloropropyltriethoxysilane
CPTMS—Chloropropyltrimethoxysilane
MPTAS—Mercaptopropyltrialkoxysilane
MPTES—Mercaptopropyltriethoxysilane
TBAB—Tetrabutylammonium Bromide
TBAC—Tetrabutylammonium Chloride
TESPD—3,3'bis(triethoxysilylpropyl)disulfide
TESPM—3,3'bis(triethoxysilylpropyl)monosulfide These and other features of the invention will become apparent from a consideration of the following detailed description.

DETAILED DESCRIPTION OF THE INVENTION

The synthesis of mercapto-functional alkoxysilanes is carried out via a reaction using a phase transfer catalysis process in an aqueous/organic medium. The use of small amounts of gases such as $H_2S$, $CO_2$, and $SO_2$, as well as the use of the other pH adjusting agents of the invention which are all acidic in nature in the aqueous phase, during the reaction, minimizes the production of undesirable end products such as TESPM and TESPD. Therefore, the yield of a mercaptopropyltrialkoxysilane can be significantly increased to more than 90 percent. As noted, it was also surprisingly discovered that a positive pressure of $H_2S$ or $CO_2$ during the reaction of (i) chloropropyltriethoxysilane with (ii) a sodium hydrosulfide solution and (iii) tetrabutylammonium bromide catalyst (TBAB) minimized TESPM and TESPD to less than 1.0 weight percent, compared to about 10 weight percent when no pressure was maintained.

In this regard, it is believed that the $H_2S$ or $CO_2$ pressure causes a reduction in the pH of the aqueous phase either by the dissolution of $H_2S$, or there occurs an intermediate reaction of $CO_2$ with $H_2O$ to form carbonic acid. In any event, at a reduced pH, the di-sodium sulfide impurities are converted to sodium hydrosulfide, and minimize TESPM formation. Thus, when a sodium hydrosulfide aqueous solution was added to a heated reactor pressurized with $H_2S$ gas and containing TBAB and CPTES, the organic phase after filtration included more than 90 weight percent of desired end product MPTES, and less than one weight percent of undesired species TESPM and TESPD.

Accordingly, the first sequence of steps of the process involves mixing a phase transfer catalyst with an haloalkylalkoxysilane. Phase transfer catalysts suitable for use according to the invention are quaternary onium cations. Some representative examples of quaternary onium salts yielding quaternary ammonium cations that can be used as phase transfer catalysts are described in U.S. Pat. No. 5,405,985 (Apr. 11, 1995), among which are tetrabutylammonium bromide (TBAB), tetrabutylammonium chloride (TBAC), tetrabutylphosphonium bromide, tetrabutylphosphonium chloride, tetraphenylarsonium bromide, and tetraphenylarsonium chloride. The '985 patent is considered as being incorporated herein by reference. The preferred quaternary onium salts according to this invention are TBAB and TBAC, most preferably TBAB. These materials are available commercially from chemical suppliers such as Sigma-Aldrich, Milwaukee, Wis. While the amount of phase transfer catalyst used in the process can vary, it is preferably used in an amount of 0.1–10 weight percent, most preferably 0.5–2 weight percent, based on the amount of haloalkylalkoxysilane being used in the process.

Haloalkylalkoxysilanes for purposes of this invention are those organosilicon compounds having a structure generally corresponding to the formula $(RO)_{3-m}R_mSi$—Alk—X, wherein each R is an independently selected hydrocarbon group containing 1–12 carbon atoms, such as methyl, ethyl, propyl, butyl, isobutyl, cyclohexyl, or phenyl. Preferably, R is a methyl or ethyl group. m can be 0, 1, or 2, but preferably m is zero. Alk represents a divalent hydrocarbon group containing 1–18 carbon atoms, preferably 2–4 carbon atoms, such as ethylene, propylene, butylene, or isobutylene. Preferably, Alk is a propylene group. X is one of the halogen atoms, i.e., fluorine, chlorine, bromine, or iodine, preferably chlorine. Some representative examples of haloalkylalkoxysilanes suitable for use in this invention include chloropropyltriethoxysilane, chloropropyltrimethoxysilane, chloroethyltriethoxysilane, chlorobutyltriethoxysilane, chloroisobutylmethyldiethoxy silane, chloroisobutylmethyldimethoxysilane, and chloropropyldimethylethoxysilane. The haloalkylalkoxysilane compound most preferred is chloropropyltriethoxysilane.

The second sequential step of the process is addition of a sulfide compound. The sulfide compound is a composition having a structure corresponding to the formula $M_2S_n$ or MHS, or mixtures thereof, wherein M represents an alkali metal or ammonium group, and H is hydrogen. While the alkali metal can be potassium, sodium, rubidium, or cesium, sodium is preferred. Representative of some preferred compositions of the type MHS include compositions such as NaHS, KHS, and $NH_4HS$, with NaHS being most preferred. The NaHS composition can be used in the form of NaHS flakes containing 71.5–74.5 weight percent NaHS, or an NaHS liquor containing 45–60 weight percent NaHS. Such materials are available commercially from PPG Industries, Inc., Pittsburgh, Pa. Optionally, compositions of the type $M_2S_n$ can be used, when it is desired to avoid the necessity of dissolving solid or flake forms. Suitable compositions of this type include $Na_2S$, $K_2S$, $Cs_2S$, $(NH_4)_2S$, $Na_2S_2$, $Na_2S_3$, $Na_2S_4$, $Na_2S_6$, $K_2S_2$ $K_2S_3$, $K_2S_4$, $K_2S_6$, and $(NH_4)_2S_2$. A particularly preferred sulfide composition is a solution containing 25–72 weight percent of NaHS, preferably 45–60 weight percent NaHS, also available from PPG Industries, Inc., Pittsburgh, Pa.

If desired, sulfur (S) can be added as an optional ingredient. A suitable sulfur is elemental sulfur in the form of an 100 mesh refined sulfur powder available from Sigma-Aldrich, Milwaukee, Wis. While the amount of sulfur and sulfide compound can vary, it can be present in a molar ratio corresponding to $S/M_2S_n$ or S/MHS of 0 to 2.0, preferably zero.

In the preferred embodiment, the phase transfer catalyst and haloalkylalkoxysilane are combined with a pH adjusting agent which is only slightly acidic in nature or one that is diluted to such an extent as to be only slightly acidic. The pH adjusting agent can be $SO_2$ (sulfur dioxide), $CO_2$ (carbon dioxide), $H_2S$ (hydrogen sulfide), $H_3PO_4$ (phosphoric acid), $H_3BO_3$ (boric acid), or HCl (hydrochloric acid). While the amount of pH adjusting agent added to the aqueous phase can vary, it is generally present in a molar amount of 0.01 to 1.0 mole per mole of $M_2S_n$ or MHS being used in the process, preferably 0.01 to 0.3 mole per mole of $M_2S_n$ or MHS being used in the process.

The process is carried out in an aqueous/organic phase containing the haloalkylalkoxysilane, phase transfer catalyst, pH adjusting agent, and sulfide compound. While the amount of water used to create the aqueous phase can vary, it is preferably based on the amount of haloalkylalkoxysilane being used in the process. The water can be added directly, or it can be present indirectly, as the water present in small amounts in starting materials. In any case, the total amount of water for purposes of the invention should include all water added directly or indirectly. Accordingly, the total amount of water used to create the aqueous phase is 1–100 weight percent of the amount of haloalkylalkoxysilane being used in the process, preferably 2.5–70 weight percent, most preferably 20–40 weight percent.

Although not being willing to be bound by any particular theory, it is believed that that the addition of only certain pH adjusting agents, i.e., the pH adjusting agents noted above, to the aqueous phase during the process, controls the pH of the reaction medium so as to directly affect product formation and minimizes any potential of undesired side reactions. Thus, the pH is controlled by addition of such pH adjusting agents at rates and concentrations so as to maintain the pH during the reaction in the range of 4 to 9, preferably in the range of 5–8, and more preferably in the range of 5 to less than 7. The haloalkylalkoxysilane compound is added to the aqueous phase at such a rate so as to control the exothermic reaction, and at the same time maintain a temperature in the range of 40–110° C. Preferably the reaction temperature is maintained at 60–95° C. The progress of the reaction can be monitored by determining the consumption of the haloalkylalkoxysilane. The amount of catalyst being used as well as the reaction temperature will affect the reaction time necessary for its completion.

At the end of the reaction, a product mixture is produced containing an organic phase, an aqueous phase, and possibly some precipitated solid materials that includes salts formed during the reaction. The organic phase contains the mercaptoalkylalkoxysilane, and separation of the mercaptoalkylalkoxysilane from the product mixture can be obtained simply by phase separation of the organic phase from the aqueous phase, or if precipitated salts are formed during the reaction, the salts can be separated first by filtering or decanting prior to the phase separation. Water or a dilute acidic solution can be added to the product mixture prior to separation, as the addition of water or a dilute acidic solution tends to enhance phase separation by dissolving precipitated salts.

The amount of water or dilute acidic solution added during this step can vary from 10–50 weight percent based on the weight of the haloalkylalkoxysilane, preferably 20–40 weight percent, and most preferably 25–35 weight percent. When a dilute acidic solution is used, it can contain HCl, $HNO_3$, or $H_2SO_4$, for example, having normal (N) concentrations of 0.000001–5, preferably 0.01–1. The dilute acidic solution can also be prepared by adding a chlorosilane to water, i.e., $\equiv$Si—Cl+H—OH→$\equiv$Si—OH+HCl.

Following addition of water or a dilute acidic solution to the product mixture, the mercaptoalkylalkoxysilane can be isolated from the product mixture by phase separating the organic phase from the aqueous phase. The organic phase containing the mercaptoalkylalkoxysilane can also be subjected to a drying step. One example of drying is to treat the organic phase under vacuum to remove any volatile organic materials present, along with the residual water. The drying can be to simply heat the organic phase to a temperature of 20–160° C. under a reduced pressure of 5–35 mm Hg (0.67 to 4.65 kPa), preferably 90–120° C. at 5–25 mm Hg (0.67 to 3.33 kPa). Alternatively, drying of the organic phase can be obtained using a thin film stripper to remove volatile organic materials as well as residual water in the organic phase.

Yet another drying technique is to contact the organic phase containing the mercaptoalkylalkoxysilane with a desiccant. The desiccant can be any solid material known to be capable of removing trace quantities of water from organic phases. Representative desiccants are typically ionic hygroscopic compositions such as sodium sulfate, magnesium sulfate, as well as the silicate based compositions such as zeolites, silica, and alumina/silicates. Preferred desiccants are sodium sulfate or magnesium sulfate, and sodium sulfate is most preferred.

The dried organic phase can then be subjected to additional steps to further improve its final purity and appearance. Thus, the organic phase containing the mercaptoalkylalkoxysilane can be heated under vacuum to strip low boiling components such as ethanol, water, tributylamine, and dissolved $H_2S$ gas, For example, the organic phase, when heated to 30–100° C. at 10–200 mm Hg/1.3–27 kPa vacuum, provides a clear product which has a better shelf life. The organic phase, after stripping the low boiling components can also be distilled under high vacuum, i.e., 1–20 mm Hg/0.133–2.7 kPa, to provide highly pure mercaptoalkylalkoxysilanes. As a result, the long-term storage stability of the mercaptoalkylalkoxysilane is enhanced, i.e., the composition does not change with time or result in products containing undesirable solid precipitates.

EXAMPLES

The following examples are set forth to illustrate the invention in more detail. In particular, they teach those skilled in the art how to obtain the primary benefits of the present invention, i.e., increase the yield of MPTES and reduce side product species such as TESPM and TESPD.

Example 1

Comparison

The purpose of this example is to show no reduction in TESPM formation when none of the pH adjusting agents of the invention are employed. Thus, in a three neck round bottom flask equipped with an addition funnel, condenser, stirrer and thermometer, was added with 100 g (1.26 moles) of NaHS flakes containing 61.7 percent by weight NaHS and 6.07 weight percent $Na_2S$, and 75.62 g of deionized (DI) water. The mixture was heated to 70° C. and mixed to make a bright yellow solution of NaHS. Then, 9.0 g (0.0094 mole) tetrabutylammonium bromide solution containing 25 weight percent active was added and mixed. The color of the mixture changed to dark brown, and an oily layer of catalyst intermediate formed at the interface. Then 317.6 g (1.32 mole) chloropropyltriethoxysilane was added slowly in 8 minutes while mixing at 500 rpm. The reaction temperature increased to 82° C. due to an exotherm. The reaction was carried out for 3 hours at 80° C., and 139.6 g of deionized water was added after cooling the mixture to 50° C. to dissolve the sodium chloride salt byproduct. After conducting a phase separation, 287.7 g of an organic phase was collected. It contained 8.4 weight percent of unreacted CPTES, 61.7 weight percent of mercaptopropyltriethoxysilane, 9.6 weight percent of TESPM, and 17.82 weight percent of TESPD, as determined by Gas Chromatograhy (GC) analysis.

Example 2

Comparison

This example is the reverse of Example 1, and shows that the product gelled. Thus, the order of addition in Example 1 was reversed, and a solution of sodium hydrosulfide flake was prepared by adding 76.2 g of water to 100.11 g of sodium hydrosulfide flakes. The solution was added slowly via an addition funnel to a reaction mixture containing 317.6 g of chloropropyltriethoxysilane and 3.1 g of solid tetrabutylammonium bromide at 67° C. The reaction mixture gelled within 5 minutes of the NaHS addition.

Example 3

Comparison

The purpose of this example is to show that while the addition of sulfur reduced the formation of TESPM, the formation of TESPD increased. Thus, in a similar reaction to the one in Example 1, the ratio of sulfur to NaHS was increased to 0.05 to convert the TESPM into TESPD. NaHS flakes (146.3 g., 1.83 mole), sulfur (2.92 g, 0.092 mole), and 100 g DI water, were mixed in a glass-jacketed reactor and heated to 70° C. TBAB solution (14.4 g, 0.011 mole) was added and mixed. Instantly, an oily omega phase was formed at the surface. CPTES (400 g, 1.66 mole) was added at a rate of about 30 ml/min. The reaction temperature increased to 94° C. due to the exotherm, and some gel was observed in the organic phase. 380.1 g (95 percent by weight of CPTES) organic phase was collected after a three hour reaction. The gas chromatography analysis showed 1.5 percent CPTES, 66.7 percent MPTES, 3.37 percent TESPM, and 27.9 percent TESPD.

Example 4

Comparison

This example is the same as Example 3 except that a salt was added so that no gelation would occur in the organic phase. However, while the formation of TESPM was reduced, the formation of TESPD increased. Accordingly, an excess amount of NaHS flakes were used, and NaCl salt was added to saturate the aqueous phase before the addition of CPTES. The sulfur/NaHS ratio was 0.05. The catalyst solution was also added after the CPTES addition was completed. Thus, NaHS flakes (100 g., 1.248 mole), NaCl 87.7 g, sulfur (2.0 g, 0.063 mole), and 161.5 g of water, were mixed and heated to 60° C. CPTES (161.5 g., 0.671 mole) was added slowly and mixed at 300 rpm. A 25 weight percent solution of TBAB catalyst was added to the reaction mixture at 65° C. A slight exotherm was observed, and the reaction was completed in about 5 hours. The GC analysis of the organic phase showed that it contained 0.35 weight percent CPTES, 62.2 weight percent MPTES, 1.1 weight percent TESPM, and 34.1 weight percent TESPD. The product was stable. The MPTES yield was less due to side reactions when sodium hydrosulfide flakes were used.

Example 5

This example shows the benefits obtained by using a solution of NaHS instead of NaHS flakes. In this example, the yield of MPTES was increased while the amount of the TESPM and TESPD byproducts decreased, by using the NaHS solution. Thus, NaHS flakes were replaced with a solution containing 45 weight percent of NaHS. No additional water was used in the aqueous phase as the NaHS solution contained water. Thus, a solution containing 45 weight percent NaHS (143 g., 1.15 mole) and 50 weight percent of a TBAB solution (99.6 g, 0.015 mole) were added into a glass reactor, mixed, and heated to 70° C. CPTES (240.8 g., 1.0 mole) was slowly added to maintain the reaction temperature below 80° C. After 5 hours, the reaction mixture was cooled to room temperature, and water was added to dissolve the NaCl salt in the aqueous phase. 229 g. of a light yellow organic phase was collected (95 weight percent based on CPTES), and analyzed. The GC analysis showed that it contained 1.6 weight percent CPTES, 84 weight percent MPTES, 6.9 weight percent TESPM, and 1.4 weight percent TESPD. No gel was found in the product. Color in the product was removed by treating it with 1–2 weight percent activated carbon black and clay.

Example 6

The NaHS/CPTES ratio in this example was changed from 1.15 to 1.30. All other conditions were similar to Example 5. An increase in rate of reaction was observed with an increase in NaHS concentration in the reaction mixture. No significant change was observed in the product composition. The reaction was completed in 3 hours. The GC analysis results showed 0.8 weight percent CPTES, 82.3 weight percent MPTES, 6.6 weight percent TESPM, and 0.8 weight percent TESPD.

Example 7

Using 45 Weight Percent NaHS Solution, Reverse Addition

Example 6 was repeated, except the order of addition of the reactants was reversed. Thus, CPTES (240.8 g., 1.0 mole) and solid TBAB (4.82 g., 0.015 mole) were added into a glass reactor, mixed, and heated to 70° C. A solution containing 45 weight percent NaHS (160.4 g., 1.30 mole) was added using an addition funnel in about 20 minutes. A slight exotherm was observed during the initial addition of NaHS. The reaction was stopped after 4 hours, and the byproduct NaCl was dissolved in water. The organic phase recovered after the phase separation was 225.5 g. (93.6 weight percent based on CPTES). The product composition by GC analysis showed that it contained 0.83 weight percent CPTES, 84.2 weight percent MPTES, 6.79 weight percent TESPM, and 0.7 weight percent TESPD. There was a slight improvement in MPTES yield by changing the order of addition of the sodium hydrosulfide. The GC analysis also showed a lower content of hydrolyzed oligomers than the GC analysis in Example 6.

Example 8

HCl as pH Adjusting Agent

The purpose of this example is to further minimize the TESPM formation and to increase the MPTES yield. Accordingly, an HCl solution was added dropwise to an NaHS solution during its reaction with CPTES at atmospheric pressure. Hydrogen sulfide gas formed in the reaction was neutralized in a caustic scrubber. 150.1 g (1.2 mole) of a 45 percent by weight NaHS solution, and 9.63 g (0.015 mole) of a 50 percent by weight TBAB catalyst solution, was added to the reactor, mixed, and heated to 65° C. 100 g (0.15 mole) of a 1.3 molar HCl solution, and 240.0 g (1.0 mole) of CPTES, were added simultaneously from two addition funnels, at a rate such that the addition of CPTES was completed in 15 minutes, and the addition of HCl was complete in about an hour. The reaction was continued at 70° C. for 5 hours. GC data showed 11.4 weight percent of unreacted CPTES remaining, and therefore 12.48 g (0.1002 mole) of an NaHS solution was again added and reacted for 5 hours. The organic phase was separated after cooling and filtered through a 0.45 micron filter disc. Gas chromatographic (GC) analysis of the organic phase showed that the product contained 2.6 weight percent of CPTES, 91.0 weight percent of MPTES, 1.99 weight percent of TESPM, and 2.34 weight percent of TESPD.

Example 9

NaHSO$_4$ as pH Adjusting Agent

A 50 percent by weight solution of NaHSO$_4$ was added to an NaHS solution during its reaction with CPTES. 325 g (2.69 mole) of an NaHS solution, and 8.2 g (0.0124 mole) of a TBAB solution, were added to a glass reactor, mixed, and heated to 75° C. The addition dropwise of NaHSO$_4$ solution was initiated just prior to the addition of CPTES. 497.8 g (2.07 mole) of CPTES was added to the reaction mixture in 8 minutes. The addition of the $NaHSO_4$ solution was complete in 30 minutes. The organic phase was separated after a 5 hour reaction and analyzed by GC. The product contained 2.0 percent by weight of CPTES, 87.6 percent by weight of MPTES, 2.7 percent by weight of TESPM, and 0.7 percent by weight of TESPD. The product was distilled under vacuum to provide a 95.4 percent pure MPTES at a yield of about 84 percent, based on the amount of CPTES employed.

Example 10

$H_3BO_3$ as pH Adjusting Agent

Boric acid was used in this example to lower the pH of the reaction mixture. The order of addition of CPTES and NaHS as compared to Example 10 was also reversed to minimize any potential formation of a gel. Thus, 206.3 g (0.86 mole) of CPTES, 4.13 g (0.013 mole) of solid TBAB, and 51.4 g (0.83 mole) of $H_3BO_3$, were mixed in a jacketed glass reactor and heated to 65° C. 100.0 g (0.83 mole) of an NaHS solution was slowly added with a dropping funnel over a time interval of 30 minutes. Froth and foaming were observed due to the reaction of NaHS and boric acid. Additional NaHS solution and TBAB catalyst were added after reaction with CPTES for 3–4 hours. After a total reaction time of 6 hours, the reaction mixture was cooled, filtered, and phase separated. The product composition by GC analysis was determined to be 1.2 percent by weight of CPTES, 89.3 percent by weight of MPTES, 2.8 percent by weight of TESPM, and 0.2 percent by weight of TESPD.

Example 11

$NaH_2PO_4$ as pH Adjusting Agent

Sodium di-hydrogen phosphate monohydrate was used as a pH adjusting agent in this example to reduce the formation of TESPM in the product. Thus, 27.6 g (0.2 mole) of $NaH_2PO_4.H_2O$ was added to a reactor. 157.4 g (1.30 mole) of a 45 percent by weight solution of NaHS was slowly added to avoid any violent reaction between NaHS and dihydrogen phosphate. $H_2S$ gas was evolved from the reaction, and was trapped in a caustic scrubber. 9.63 g (0.015 mole) of a TBAB solution was added, and mixed for 5 minutes. A very dark green omega phase of a catalyst intermediate formed instantly. The reaction mixture was slowly heated to 70° C., and 240.8 g (1.0 mole) of CPTES was added over 15 minutes. The reaction was continued for 4 hours at 70° C. Upon its cooling and phase separation, a 227.6 gram organic phase was obtained. The organic phase yield was 94.5 percent, based on the amount of CPTES used in the reaction. GC results of the organic phase showed 2.8 percent of CPTES, 89.6 percent of MPTES, 4.5 percent of TESPM, and 1.15 percent of TESPD.

Example 12

$NaO(O)CH_3$ as pH Adjusting Agent

In this example, sodium acetate trihydrate was mixed with an NaHS solution to reduce the pH of the aqueous phase and to minimize the formation of TESPM. Thus, equimolar amounts of sodium acetate and NaHS were added to a reactor and mixed. No change in the pH was observed. The reaction was carried out using a slight molar excess of CPTES, and in the presence of the TBAB catalyst, as described above in Examples 8–11. GC results of the final product showed no effect on TESPM reduction, however. The product contained 83.1 percent by weight of MPTES and 7.38 percent by weight of TESPM.

In the following examples, a series of experiments were performed using $H_2S$ as pH adjusting agent, at different $H_2S$ pressure, to control the pH of reaction mixture and improve the yield of MPTES.

Example 13

10 psi/69 kPa—Normal Addition

A pressure reactor containing NaHS solution was pressurized with $H_2S$ gas to 10 psi at room temperature before reacting it with CPTES in presence of a TBAB catalyst. The $H_2S$ gas in water had a pH of 4.2, and reacted with $Na_2S$ byproducts in the aqueous phase to provide NaHS. It also prevented $Na_2S$ formation by maintaining the pH below 9. The positive pressure of $H_2S$ during the reaction also minimized hydrolysis of any alkoxy groups and polymer formation Thus, 139.4 g (1.15 mole) of NaHS solution was added to the reactor and the reactor was sealed. The reactor was then charged with 10 psi/69 kPa $H_2S$ and the contents were mixed for 5 minutes. A pressure drop was initially observed due to the $H_2S$ solubility in water and its reaction with $Na_2S$. The NaHS was heated to 70° C., and 9.6 g (0.015 mole) of a 50 weight percent solution of TBAB and 240.8 g (1.0 mole) of CPTES were fed consecutively into the reactor using a pressure syringe. The reaction was continued for 3.5 hours at 80° C. before being cooled. Deionized water was added to the reaction mixture to dissolve any NaCl salt byproduct, and the organic phase was recovered by phase separation. The GC composition consisted of 1.8 weight percent of CPTES, 87.5 weight percent of MPTES, 4.6 weight percent of TESPM, and 1.5 weight percent of TESPD. The yield was 90 percent.

Example 14

50 psi/345 kPa—Normal Addition

Except for the 50 psi/345 kPa $H_2S$ pressure, all other conditions were the same as Example 13. The reaction was completed in 5 hours. The product composition was 0.4 weight percent of CPTES, 93.0 weight percent of MPTES, 1.9 weight percent of TESPM, and 0.08 weight percent of TESPD. The product yield was 93.3 percent.

Example 15

100 psi/690 kPa—Normal Addition

Except for the 100 psi/690 kPa $H_2S$ pressure, all other conditions were the same as Examples 13 and 14. The product composition after a 5 hour reaction was 0.5 weight percent of CPTES, 89.8 weight percent of MPTES, 0.8 weight percent of TESPM, and 0.3 weight percent of TESPD. The yield was 95.3 percent. It can be seen that the yield of MPTES was improved by suppressing any byproduct formation through control of the pH by the $H_2S$ gas.

Example 16

50 psi/345 kPa—Reverse Addition

This example is the same as Example 14 except that the order of addition of the reactants is reversed. Also, a solid TBAB catalyst was used to avoid the hydrolysis of CPTES. Thus, 240.8 g (1.0 mole) of CPTES and 4.8 g (0.015 mole) of solid TBAB catalyst were loaded into a pressure reactor and the reactor was sealed. The reactor was pressurized with $H_2S$ until the pressure stabilized at 50 psi/345 kPa. The $H_2S$ valve was closed, and the reaction mixture was heated to 70° C. while mixing the contents at 500 rpm. 139.2 g (1.15 mole) of an NaHS solution was then slowly added to the reactor at a rate of about 10 ml/min using a pressure syringe pump. The reaction temperature increased to 80° C. due to the exothermic reaction. After 5 hours of reaction at 80° C., the mixture was cooled to 30° C. and any salt byproducts were dissolved in 69 g of deionized water. Upon cooling and phase separation, a 229 gram organic phase was obtained. The organic phase yield was 95.4 percent based on the amount of CPTES used in the reaction. GC results of the organic phase showed 0.9 percent of CPTES, 93.3 percent of MPTES, 0.4 percent of TESPM, and 1.0 percent of TESPD. Thus, it can be seen that the yield of MPTES was increased when $H_2S$ gas was used in this example of a reverse addition process.

In the following examples, a series of experiments were performed using $CO_2$ as the pH adjusting agent, at different $CO_2$ pressure, to control the pH of reaction mixture and improve the yield of MPTES.

Example 17

25 psi/173 kPa—Normal Addition

A pressure reactor containing an NaHS solution was pressurized with $CO_2$ gas to 25 psi/173 kPa at room temperature before reacting it with CPTES in presence of a TBAB catalyst. The $CO_2$ gas in water was slightly acidic due to the formation of carbonic acid, which in turn reacts with any $Na_2S$ byproduct in the NaHS solution to minimize TESPM formation, and to improve the overall yield of MPTES. Maintaining a positive pressure of $CO_2$ during the reaction also minimized any hydrolysis of alkoxy groups and polymer formation.

Thus, and similar to Example 12, 139.2 g (1.15 mole) of an NaHS solution was charged to the pressure reactor and the reactor was sealed. 10 psi/69 kPa $CO_2$ pressure was applied and the contents were mixed for 5 minutes. The reaction mixture was heated to 70° C. and 9.6 g (0.015 mole) of a TBAB solution and 240.8 g (1.0 mole) of CPTES were added to the reactor by a pressure syringe at a controlled rate. The reaction was continued for 5 hours at 80° C. The progress of the reaction was monitored by the GC analysis of the organic phase and the consumption of CPTES. After cooling the reaction mixture and phase separation, the organic phase was stripped to remove any low boilers and analyzed by GC. The product contained 0.3 weight percent of CPTES, 92.1 weight percent of MPTES, 2.3 weight percent of TESPM, and 0.5 weight percent of TESPD. The yield was 91.1 percent based on the amount of CPTES used.

Example 18

50 psi/345 kPa—Normal Addition

Except for $CO_2$ pressure being increased to 50 psi/345 kPa, all other conditions were the same as Example 16. After phase separation, the organic phase was analyzed by GC, and it contained 0.5 weight percent of CPTES, 88.8 weight percent of MPTES, 1.3 weight percent of TESPM, and 2.6 weight percent of TESPD. Similar good results were obtained when the $CO_2$ was continuously fed to the reactor during a reaction at 50 psi/345 kPa.

Example 19

100 psi690 kPa—Normal Addition

Example 18 was repeated, except that the reaction was performed at 100 psi/690 kPa $CO_2$ pressure. The pressure increased to 135 psi/932 kPa when the reaction mixture was heated to 70° C. The pressure dropped during the CPTES addition as the NaHS was consumed in the reaction. The organic phase was isolated after completion of the reaction and analyzed. The product contained 2.3 weight percent of CPTES, 88.2 weight percent of MPTES, 0.9 weight percent of TESPM, and 2.8 weight percent of TESPD. Color in the product was removed by treatment with activated carbon black.

Example 20

50psi/345 kPa—Reverse Addition

Example 16 was repeated, except that the reaction was carried out under a 50 psi/345 kPa $CO_2$ gas pressure. NaCl and $NaHCO_3$ salts were produced in the reaction. Upon cooling and phase separation, a 222.8 gram organic phase was obtained. The organic phase yield was 92.8 percent based on the amount of CPTES used in the reaction. GC results of the organic phase showed 0.8 percent of CPTES, 92.4 percent of MPTES, 1.2 percent of TESPM, and 0.5 percent of TESPD. The organic phase was also distilled under vacuum, and the product was collected at 68° C./1 mm Hg/0.133 kPa. After complete distillation, a small amount of solid polymer residue remained in the pot. The distillate contained 0.9 weight percent of CPTES and 98.0 weight percent of MPTES.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A process for making mercaptoalkylalkoxysilanes comprising the sequential steps of:
    first, mixing (i) a pH adjusting agent and (ii) a sulfide containing compound of the formula $M_2S_n$ or MHS where M is an alkali metal or an ammonium group and H is hydrogen, in an aqueous phase, to provide a pH in the range of 4–9 of the aqueous phase,
    second, adding (iii) a phase transfer catalyst to the aqueous phase,
    third, adding (iv) a haloalkylalkoxysilane to the aqueous phase, to form a reaction mixture containing mercaptoalkylalkoxysilanes and water soluble byproducts, and
    fourth, separating the desired mercaptoalklyalkoxysilanes from the water soluble byproducts.

2. The process according to claim 1 in which the pH adjusting agent is sulfur dioxide, carbon dioxide, hydrogen sulfide, phosphoric acid, boric acid, or hydrochloric acid.

3. The process according to claim 2 in which the pH adjusting agent is carbon dioxide or hydrogen sulfide.

4. The process according to claim 3 in which the pressure of the carbon dioxide or hydrogen sulfide is 10–200 psi/69–1,380 kPa.

5. The process according to claim 4 in which the pressure is 25–100 psi/173–690 kPa.

6. The process according to claim 1 in which the pH in the aqueous phase is 5–8.

7. The process according to claim 6 in which the pH in the aqueous phase is 5 to less than 7.

8. The process according to claim 1 in which the reaction temperature is 40–110° C.

9. The process according to claim 8 in which the reaction temperature is 60–95° C.

10. The process according to claim 1 in which the haloalkylalkoxysilane has the formula $(RO)_{3-m}R_mSi$—Alk—X wherein each R is a hydrocarbon group containing 112 carbon atoms; m is 0, 1, or 2; Alk represents a divalent hydrocarbon group containing 1–18 carbon atoms; and X is chlorine, bromine, or iodine.

11. The process according to claim 10 in which the haloalkylalkoxysilane is chloropropyltriethoxysilane, chloropropyltrimethoxy silane, chloroethyltriethoxysilane, chlorobutyltriethoxy silane, chloroisobutylmethyldiethoxysilane, chloroisobutylmethyldimethoxy silane, or chloropropyldimethylethoxysilane.

12. The process according to claim 11 in which the haloalkylalkoxysilane is chloropropyltriethoxysilane.

13. The process according to claim 1 in which the sulfide-containing compound is sodium hydrosulfide, potassium hydrosulfide, or ammonium hydrosulfide, disodium sulfide, dipotassium sulfide or diammonium sulfide.

14. The process according to claim 13 in which the sulfide-containing compound is sodium hydrosulfide.

15. The process according to claim 14 in which the sodium hydrosulfide is an aqueous solution containing 25–72 percent of sodium hydrosulfide.

16. The process according to claim 15 in which the aqueous solution contains 40–50 percent of sodium hydrosulfide.

17. The process according to claim 1 in which the phase transfer catalyst is a quaternary onium salt.

18. The process according to claim 17 in which the phase transfer catalyst is tetrabutylammonium bromide, tetrabutylammonium chloride, tetrabutylphosphonium bromide, tetrabutylphosphonium chloride, tetraphenylarsonium bromide, or tetraphenylarsonium chloride.

19. The process according to claim 18 in which the phase transfer catalyst is tetrabutylammonium bromide.

20. The process according to claim 1 in which the aqueous phase is saturated with sodium chloride.

21. The process according to claim 1 in which the aqueous phase in the first step of the process is free of sodium chloride.

22. A process for making mercaptoalkylalkoxysilanes comprising the sequential steps of:

first, mixing together (i) a haloalkylalkoxysilane, (ii) a phase transfer catalyst, and (iii) an anhydrous pH adjusting agent, second, adding an aqueous solution of a sulfide containing compound or mixture of compounds of the formula $M_2S_n$ or MHS where M represents an alkali metal or ammonium group and H represents hydrogen, to form an aqueous reaction mixture with a pH in the range of 4–9 containing mercaptoalkylalkoxysilanes and water soluble byproducts, and third, separating the desired mercaptoalklyalkoxysilanes from the water soluble byproducts.

23. The process according to claim 22 in which the pH adjusting agent is sulfur dioxide, carbon dioxide, hydrogen sulfide, phosphoric acid, boric acid, or hydrochloric acid.

24. The process according to claim 23 in which the pH adjusting agent is carbon dioxide or hydrogen sulfide.

25. The process according to claim 24 in which the pressure of the carbon dioxide or hydrogen sulfide is 10–200 psi/69–1,380 kPa.

26. The process according to claim 25 in which the pressure is 25–100 psi/173–690 kPa.

27. The process according to claim 22 in which the pH is 5–8.

28. The process according to claim 27 in which the pH is 5 to less than 7.

29. The process according to claim 22 in which the reaction temperature is 40–110° C.

30. The process according to claim 29 in which the reaction temperature is 60–95° C.

31. The process according to claim 22 in which the haloalkylalkoxysilane has the formula $(RO)_{3-m}R_mSi$—Alk—X wherein each R is a hydrocarbon group containing 1–12 carbon atoms; m is 0, 1, or 2; Alk represents a divalent hydrocarbon group containing 1–18 carbon atoms; and X is chlorine, bromine, or iodine.

32. The process according to claim 31 in which the haloalkylalkoxysilane is chloropropyltriethoxysilane, chloropropyltrimethoxy silane, chloroethyltriethoxysilane, chlorobutyltriethoxy silane, chloroisobutylmethyldiethoxysilane, chloroisobutylmethyldimethoxy silane, or chloropropyldimethylethoxysilane.

33. The process according to claim 32 in which the haloalkylalkoxysilane is chloropropyltriethoxysilane.

34. The process according to claim 22 in which the sulfide-containing compound is sodium hydrosulfide, potassium hydrosulfide, or ammonium hydrosulfide, disodium sulfide, dipotassium sulfide or diammonium sulfide.

35. The process according to claim 34 in which the sulfide-containing compound is sodium hydrosulfide.

36. The process according to claim 35 in which the aqueous solution contains 25–72 percent of sodium hydrosulfide.

37. The process according to claim 36 in which the aqueous solution contains 40–50 percent of sodium hydrosulfide.

38. The process according to claim 22 in which the phase transfer catalyst is a quaternary onium salt.

39. The process according to claim 38 in which the phase transfer catalyst is tetrabutylammonium bromide, tetrabutylammonium chloride, tetrabutylphosphonium bromide, tetrabutylphosphonium chloride, tetraphenylarsonium bromide, or tetraphenylarsonium chloride.

40. The process according to claim 39 in which the phase transfer catalyst is tetrabutylammonium bromide.

41. The process according to claim 22 in which the aqueous reaction mixture is saturated with sodium chloride.

42. The process according to claim 22 in which the mixture in the first step of the process is free of sodium chloride.

* * * * *